United States Patent
Pind et al.

(10) Patent No.: US 7,208,091 B2
(45) Date of Patent: Apr. 24, 2007

(54) ASSEMBLY FOR WITHDRAWING AND FILTERING PARTIAL VOLUMES OF PROCESS FLUID

(75) Inventors: Peter Frode Pind, Gentofte (DK); Birgitte Kiaer Ahring, Hoersholm (DK)

(73) Assignee: Bio Gasol IPR APS, Hoersholm (DK)

( * ) Notice: Subject to any disclaimer, the term of this patent is extended or adjusted under 35 U.S.C. 154(b) by 0 days.

(21) Appl. No.: 10/312,455

(22) PCT Filed: Jun. 26, 2001

(86) PCT No.: PCT/DK01/00447

§ 371 (c)(1), (2), (4) Date: Apr. 22, 2003

(87) PCT Pub. No.: WO02/00324

PCT Pub. Date: Jan. 3, 2002

(65) Prior Publication Data

US 2003/0160007 A1    Aug. 28, 2003

(51) Int. Cl.
B01D 33/06    (2006.01)
B01D 61/00    (2006.01)

(52) U.S. Cl. .......... 210/645; 210/650; 210/784; 210/797; 210/321.68; 210/321.87; 210/402; 73/64.56; 73/863.23; 73/863.24

(58) Field of Classification Search .......... 73/64.56, 73/863.23, 863.24, 645, 650, 780, 797, 798, 73/196, 321.63, 321.68, 321.87, 359, 391, 73/398, 402, 406, 407, 409, 416.1; 210/473, 210/474

See application file for complete search history.

(56) References Cited

U.S. PATENT DOCUMENTS

| 3,669,879 A | * | 6/1972 | Berriman | 210/652 |
| 3,997,447 A | | 12/1976 | Breton et al. | |
| 4,647,376 A | * | 3/1987 | Galaj | 210/297 |
| 4,695,551 A | * | 9/1987 | Samhaber et al. | 73/863.23 |
| 4,713,176 A | * | 12/1987 | Schoendorfer et al. | 210/645 |
| 4,790,942 A | * | 12/1988 | Shmidt et al. | 210/650 |
| 4,876,013 A | | 10/1989 | Shmidt et al. | |
| 4,897,192 A | | 1/1990 | Lawrence | |
| 4,952,317 A | * | 8/1990 | Culkin | 210/636 |
| 5,194,145 A | * | 3/1993 | Schoendorfer | 210/90 |
| 5,888,748 A | * | 3/1999 | Crabb et al. | 435/7.3 |
| 5,944,998 A | | 8/1999 | Rolchigo et al. | |
| 6,123,841 A | * | 9/2000 | Gotoh | 210/169 |
| 6,416,665 B1 | * | 7/2002 | McGrath | 210/321.67 |
| 2003/0160007 A1 | * | 8/2003 | Pind et al. | 210/784 |
| 2003/0175851 A1 | * | 9/2003 | Pind et al. | 435/34 |

FOREIGN PATENT DOCUMENTS

DE    3426742    1/1986
DE    196-25-428 C2    9/1998

* cited by examiner

Primary Examiner—Robert James Popovics
(74) Attorney, Agent, or Firm—Budde, Schou & Ostenfeld A/S; Robert C. Casad

(57) ABSTRACT

A method for withdrawing and filtering a partial volume of a particle-containing process fluid enclosed in a container, a combination of a container enclosing a process fluid and an assembly for continuously withdrawing and filtering a partial volume of a process fluid and a cross-flow filtering device are disclosed. The method, the assembly and the filtering device can be used in connection with biological process systems, in which the removal of sand, sludge, fibers and alike from partial volumes of the process fluid is necessary before additional filtration and subsequent sample analysis.

7 Claims, 4 Drawing Sheets

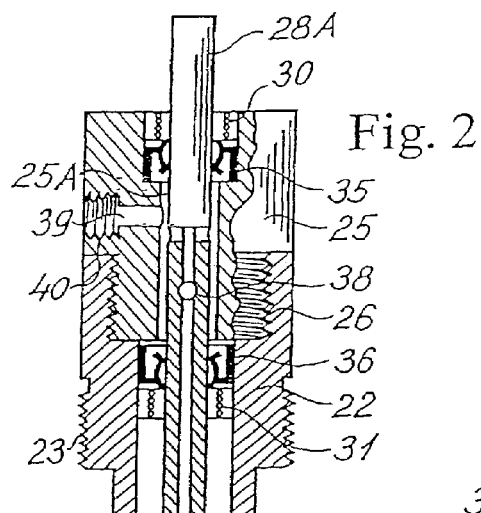
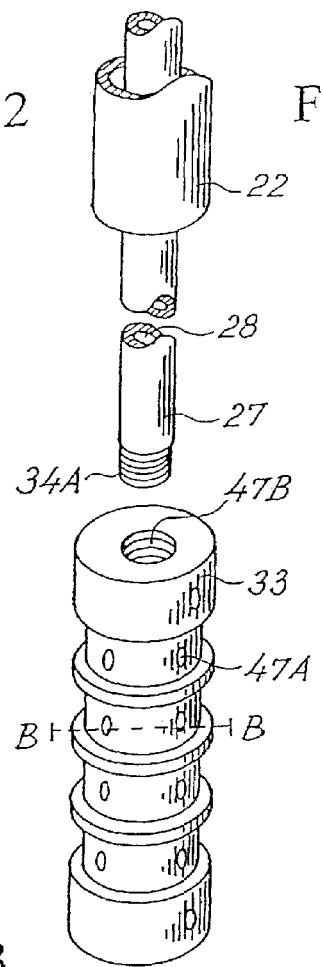
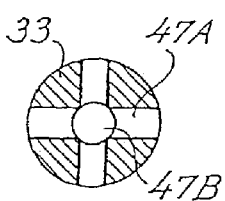
Fig. 3A
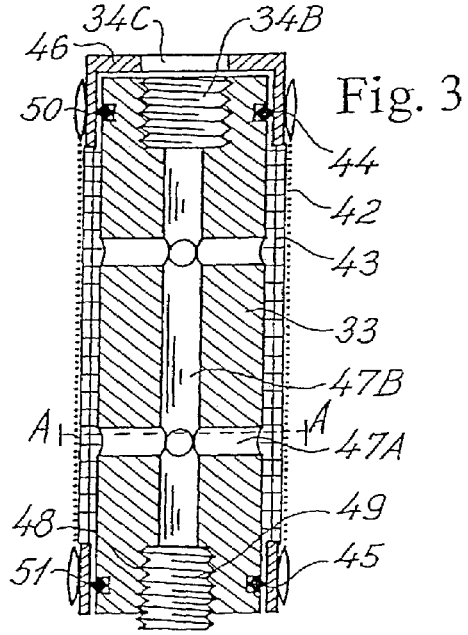
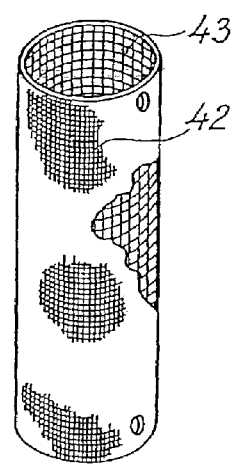
Fig. 4A

ASSEMBLY FOR WITHDRAWING AND FILTERING PARTIAL VOLUMES OF PROCESS FLUID

FIELD OF THE INVENTION

The present invention relates to a method and an assembly for withdrawing and filtering a partial volume of a process fluid enclosed in a container, and primarily concerns assemblies providing essentially continuous withdrawal and filtration of partial volumes of a biological process fluid, e.g from an anaerobic digestion, directly from the container enclosing the fluid, while avoiding a substantial reduction in the flow of filtered process fluid with time, and avoiding the need for repeated interruption of the filtering process in order to clean the filter medium or to dislodge filter cake collecting on the filter medium. More specifically the present invention relates to a method and an assembly for continuously withdrawing and filtering small volumes of a biological process fluid containing particles, e.g. for on-line determination of the content of a suitable parameter reflecting the metabolic state of the process in the process fluid, directly from a biological process plant.

BACKGROUND OF THE INVENTION

Increasing industrial application of biological process fluids, such as in waste water treatment and biological gas production, has resulted in a need for development of reliable methods for evaluation and control of the considered biological process, e.g. the anaerobic digestion process.

Monitoring of the process first of all requires access to a suitable parameter reflecting the metabolic state of the process. Secondly, it requires a system providing reliable determination of this process parameter in order to obtain efficient control, with the shortest possible delay, between process failure and operator response.

At present, measurements of suitable parameters reflecting the metabolic state of biological processes, such as waste water treatment and biological gas production, are only used to a limited extent. This is due to several factors, one of which is that filtering adequate volumes of the process fluid from a biological process, e.g. an anaerobic digestion, offers a series of problems. Most such process fluids have a high content of organic fibers, inhomogenous particles, and dissolved fats, which gives them wearing and clogging properties making them unsuitable for traditional membrane filtration. Furthermore, the high content of inhomogenous particles in these process fluids, makes it difficult to remove all particles with a diameter larger than acceptable for most analytical equipment through continuous one-step filtration, without employing very large quantities of process fluid. At present this renders the currently available methods uneconomical.

As described above, the on-line recovery of a limited amount of filtrate that can be employed in the analysis is one of the main problems when trying to develop methods for evaluation and control of biological processes, such as anaerobic digestion. The mere separation of solids from fluids is a problem faced in a diverse range of processing situations. Interestingly, the same principles that govern mineral separation in huge froth flotation plants handling millions of tons of ore also apply to separations carried out in laboratories on centiliters of a raw solution using the most sophisticated equipment. Further, the same principles apply to separations of true solutions with no particles involved (e.g., solutions with dissolved molecules such as salts, proteins, etc.). Of course, the filter media and the process conditions are different, but the basic principles are the same.

Some of the most widely described and used filtration processes are those involving porous membranes. The fluid containing solid particles passes through the pores in the membrane, and the particles are trapped on the retentate side of the filter surface. A wide variety of membrane types are available on the market. They vary by material as well as by pore size. Membranes may be woven or non-woven metallic thread, ceramic, plastic, cloth or a hybrid of two or more materials. Whatever the membrane material, the operation of the membrane can be characterized by a number of parameters, including construction, performance, pore size and porosity.

For efficient operation, the pore size of the membrane filter surface must be less than the size of the smallest particles to be removed. If these criteria are met the fluid will flow through the membrane but the particles will be captured. After a period of time the increasing amount of trapped solids will block the pores of the membrane and prevent or restrict the flow of fluid, and in turn this will lead to the main disadvantage when employing this type of filtration, namely clogging of the pores.

Once the flow of fluid through the filter is reduced below acceptable levels it is necessary to clean the filter. When using prior art filtration techniques, the filtering medium is typically cleaned for reuse by mechanical removal of solids or by backflushing. Obviously, normal filtration operations must be suspended during the cleaning operation. When backflushing, a fluid, usually water containing detergents or a suitable solvent for the solids, is passed in a reverse direction through the filter to dislodge and remove solid particles from the pores of the filtering medium after the medium has become fully or partially plugged. The disruption is minimized if the back flushing is a simple reversal of the filtration operation but more often back flushing involves a different process. Many back flush operations require steam or compressed air to be directed back through the filter. This leads to a complex system for performing all the required operations.

As noted above, the clogging or blinding of filter media is a problem at any level of filtration, insofar as the transmembrane flow drops as the pores in the filter media become clogged. While scraping off a filter cake and backflushing the canvas will suffice in simple flotation separations, the problems multiply when one deals with finer separations and in particular if one deals with an assembly for continuously withdrawing and filtering partial volumes of a process fluid containing inhomogenous particles.

In view of the foregoing it would be helpful, when considering the development of reliable methods for evaluation and control of biological processes, such as anaerobic digestion processes, to have access to a method and an assembly for continuously withdrawing and filtering partial volumes of the process fluid, directly from the container holding it and removing all particles with a diameter larger than acceptable for the analytical equipment employed. However, as will also be understood from the above, the development of an assembly for continuously in situ filtering the process fluid from biological processes, e.g. anaerobic digestions, poses several problems, since this necessitates the filtering of small quantities of process fluid with a high content of relatively large inhomogenous particles.

One known way of overcoming the deficiencies of the traditional dead end filtration described above, is by feeding fluid across a membrane from an inlet port to an outlet port, known as cross flow filtration. Filtrate is then drawn through the membrane to a filtrate outlet port. Because the feed fluid flows across the surface of the membrane the amount of material trapped permanently in the pores of the membrane is reduced. Essentially, the principle behind the inherent selfcleaning of the filtermaterial utilized in traditional cross flow techniques, would be applicable for on line filtration of biological process fluids, assuming that an appropriate system for continuously filtering and recirculating process fluid to the process fluid could be constructed. However, ordinarily cross flow filtration depends on a linear flow rate of at least 0.5–1 m/sec in order to function properly, which necessitates the use of either very narrow tubing dimensions or high capacity pumps. This is a serious limitation to this procedure, when considering biological process fluids, since these tend to have a high content of inhomogenous particles. Thus, the tubing size actually needed to avoid filter clogging severely limits the kind of fluids that can be filtered by traditional cross flow methods without the use of very large tubing dimensions. In particular process fluids with a high content of organic fibers, crystalline particles, and dissolved fats, such as the process fluid from an anaerobic digestion, have wearing and clogging properties, which would necessitate tubing resulting in the handling of large quantities of process fluid. At present this makes the currently available cross flow methods uneconomical for continuously filtering a biological process fluid containing inhomogenous particles.

Another known way of overcoming filter clogging is by employing one or several rotating parts in the filtration apparatus. U.S. Pat. Nos. 4,876,013 and 4,790,942 describe methods and various assemblies for filtration, employing an inner body rotating within a stationary outer body, on which either or both a membrane is mounted. Here attempts are made to overcome the clogging problem by making use of a hydrodynamic phenomena known as Taylor vortices, which is created in the parent fluid in the narrow gap between the bodies by the rotation. Parent fluid is feed to the gap between the cylinder surfaces, and the fluid is filtered through the membrane(s) during rotation of the inner or both cylinders, and means are provided to lead permeate from the membrane to a collection point. A serious limitation to these procedures within the present context is that they rely on an outer body within or along with, which the inner body or membranes can rotate. This puts severe limitations on the character and size of the particles contained in the fluids, which can be filtered employing this method. In particular, process fluids with a high content of organic fibers, crystalline particles, and dissolved fats, e.g. the process fluid from an anaerobic digestion, have wearing and clogging properties making them unsuitable for this type of filtration, since the content of inhomogenous particles in these process fluids would inevitably hinder the access of process fluid to the processing zone in the narrow gap. Furthermore the filtering assemblies described in U.S. Pat. Nos. 4,876,013 and 4,790, 942 are, when they are to be used for continuous filtration, connected to the container holding the process fluid by tubing and can per se not be considered as true build in assemblies. Furthermore, as with the traditional cross flow techniques described above, the tubing size actually needed to avoid filter clogging severely limits the kind of fluids, which can be filtered by this method without the use of very large tubing dimensions. In particular, process fluids with a high content of organic fibers, crystalline particles, and dissolved fats, such as the process fluid from an anaerobic digestion, have wearing and clogging properties, which would necessitate tubing resulting in the handling of large quantities of process fluid.

U.S. Pat. No. 3,997,447 describes another known kind of rotary filtration structures, comprising high speed rotating disc filtration devices. This patent describes a plurality of filter discs mounted on a rotatable hollow shaft having a plurality of radial openings. The shaft is mounted for high speed rotation in a vessel or chamber which remains stationary. The fluid suspension to be filtered is admitted directly into the vessel, which indicates that the process is per se not applicable in situ, since it requires a restricted feed flow to the filtration vessel. The filtration surfaces rotate through the fluid suspension, and filtrate flows through the surfaces into the core of the filter. The filtrate flows from the filter core through the radial openings in the shaft into the fluid channels in the rotating shaft, and is then conducted out through the fluid channels for collection outside the vessel. However, when employing rotating filter discs, the fluid suspension must be in a processing zone, which is located between the shaft and the tips of the spinning discs. To gain access to this processing zone, the fluid suspension must flow radially inward past the tips and against the flow direction of solids and fluids, which are thrown radially outward from the shaft by centrifugal forces. A potential solution to this drawback is pointed out in U.S. Pat. No. 4,897,192, which describes a method similar to U.S. Pat. No. 3,997,447 apart from the fact that the process fluid to be filtered is feed to the space between two rotating discs under pressure. However, this procedure would not be applicable when handling most biological process fluids with a high content of inhomogenous particles, since as above the need for tubing seriously limits the kind of fluids, which can be filtered by this method. Hence, e.g. the process fluid from an anaerobic digestion would be unsuitable for this type of filtration.

The use of submerged tube shaped filters or filtration modules for treating process fluids is described in DE 196 25 428. The mode of operation described involves sequential filtration, which may employ rotating tube shaped filters or filtration modules for ultra- or nanofiltration. Since the method described comprises sequential submersion of the filtration module into the container holding the process fluid, the assemblies described can not be considered as permanently attached to the container and would not be suited for online filtration of partial volumes of process fluids with a high content of organic fibers, crystalline particles, and dissolved fats, e.g. the process fluid from an anaerobic digestion or of process fluids under pressure.

In conclusion all of the above mentioned prior art methods would depend either on a batch, semi-batch or at least partially off line approach in order to obtain proper filtration of small quantities of a process fluid with a high content of organic fibers, crystalline particles, and dissolved fats, such as the process fluid from an anaerobic digestion. Furthermore, when employing most of the methods there would be a need for tubing connecting the filtering device of choice to the process fluid. This would result in the handling of large quantities of process fluid, when these have a high content of organic fibers, crystalline particles, and dissolved fats, such as the process fluid from an anaerobic digestion. Hence, no means for a true on line or build in one step continuous filtration of biological process fluids with a high content of inhomogenuos particles is currently available.

SUMMARY OF THE INVENTION

In general the present invention provides a method for withdrawing and filtering a partial volume of a particle-containing process fluid enclosed in a container, and also a combination of a container enclosing a process fluid and an assembly for continuously withdrawing and filtering a partial volume of said process fluid. The method and assembly can be used with biological process systems, in which the removal of sand, sludge, fibbers and alike from partial volumes of the process fluid is necessary before additional filtration and subsequent sample analysis. By employing a steady pump flow on the filtrate side of the assembly, the flow of filtered process fluid can be controlled. By this, the volume withdrawn can be controlled and reduced to what is needed for an optional subsequent analysis. The running and performance of the assembly can be monitored by measuring the pressure differential between the filter and the applied pump, in which case a sudden pressure drop during continuous operation would indicate that the filtering device is starting to clog.

Compared to prior art equipment and methods the combination of a container holding a process fluid and the build in assembly of the present invention provides a means for continuously obtaining a filtrate that can be employed in the analysis of a suitable parameter, e.g. the content of volatile fatty acids, reflecting the metabolic state of a biological process, e.g. an anaerobic digestion, thus enabling the shortest possible delay between process failure and operator response without handling large quantities of process fluid,
depending on a batch or semi-batch driven approach in order to function properly,
relying on a stationary outer body in which the filtering screen can rotate.

It is an object of the present invention to provide a method, and an assembly combined with a container holding a process fluid, for continuously filtering and withdrawing partial volumes of biological process fluids containing particles with a diameter larger than about 0.1% to about 1% of the desired linear flow rate of filtered process fluid pr. second through the filtering screen.

A further object of the present invention is to provide an easily maintainable build in assembly for withdrawing and filtering partial volumes of process fluids from biological processes, e.g. an anaerobic digestion, enabling measurements of suitable parameters reflecting the metabolic state of said biological processes.

Another object of the present invention is to provide a filtering device for use in such an assembly for such purposes in which the filtering screen is maintained in an unclogged state during normal operation.

Another object of the invention is to provide an assembly capable of providing a desired amount of filtered process fluid, without treating inexpedient large quantities of process fluid.

Still other objects and advantages of the invention will appear from the following description.

According to the present invention these objects are obtained by a method for continuously withdrawing and filtering a partial volume of a particle-containing process fluid enclosed in a container, the method comprising the following steps:

providing an aperture in a wall of the container,
providing a filtering device having a filtering screen with a filter surface being rotationally symmetrical about an axis of rotation, withdrawing means for withdrawing filtered process fluid and rotating means for rotating said surface around said axis,
fixing said filtering device in said aperture such that the filtering screen is immersed in said process fluid,
establishing a pressure differential through said filtering screen for causing said process fluid to flow therethrough to said withdrawing means,
rotating said surface around said axis, while ensuring free access of said process fluid to at least a portion of said surface.

In the currently most preferred embodiment of the method according to the present invention said filter surface is rotated around said axis at a speed sufficient to cause at least a substantial area of said surface to move at a tangential speed of at least approx. 0.3 meters/second, preferably approx. 0.4 meters/second, more preferably approx. 0.5 meters/second, even more preferably approx. 0.6 meters/second, even more preferably approx. 0.7 meters/second, even more preferably approx. 0.8 meters/second, even more preferably approx. 0.9 meters/second and even more preferably approx. 1.0 meters/second.

The currently preferred embodiment of the method according to the present invention further comprises the steps of:

providing a fluid lock mechanism for isolating said filtering screen from said process fluid in a compartment in said mechanism, the compartment communicating with one or more apertures allowing access to said screen for cleaning and maintenance of said filtering screen,
fixing said filtering device in said aperture by the means of said fluid lock mechanism.

By providing a fluid lock mechanism, the method according to the present invention enables easy cleaning and maintenance of the filtering screen without totally disconnecting it from the container holding the process fluid. In this way it ensures that any potential contamination of the process fluid or uncontrolled release of process fluid from the container is avoided. Furthermore it enables the removal of the filtering screen from the container, with only a minimal disturbance of the conditions prevailing in the process fluid.

In the currently most preferred embodiment of the method according to the present invention it further comprises the steps of isolating said filtering screen in said compartment and cleaning said screen with a fluid such as hot water supplied through one of said apertures, the fluid optionally being made acidic or alkaline by addition of acid or base, respectively.

In a particularly preferred embodiment of the method according to the present invention the filter surface is substantially circular cylindrical.

Providing and rotating a circular cylindrical filter surface in a process fluid will ensure that a substantial degree of process fluid cross flow relative to the filter surface occurs, i.e. a circular cylindrical filter surface is especially suited for enabling cross flow filtration and thereby for preventing filter clogging.

Moreover, in a preferred embodiment of the method according to the present invention filter clogging is prevented by ensuring that the linear velocity of the fluid through the filtering screen is less than said tangential speed at the desired flow rate of filtered process fluid, so as to ensure a corresponding cross flow velocity of the fluid to be filtered relative to said surface for preventing obstruction of said pores.

Advantageously, the difference between said linear velocity of the fluid and said tangential speed preventing filter clogging is at least approx. 0.2 meters/second, preferably approx. 0.3 meters/second, more preferably approx. 0.4 meters/second, even more preferably approx. 0.5 meters/second, even more preferably approx. 0.6 meters/second, even more preferably approx. 0.7 meters/second, even more preferably approx. 0.8 meters/second, even more preferably approx. 0.9 meters/second, and even more preferably approx. 1.0 meters/second.

In a particularly preferred embodiment of the method according to the present invention said process fluid is a biological process fluid such as the process fluid from a biological gas plant.

Furthermore, according to the present invention the objects mentioned above ar obtained by a combination of a container enclosing a particle-containing process fluid, and an assembly for withdrawing and filtering a partial volume of said process fluid, the assembly comprising:
 a filtering device having a filtering screen with a filter surface being rotationally symmetrical about an axis of rotation, withdrawing means for withdrawing filtered process fluid and rotating means for rotating said surface around said axis, the container comprising:
 an aperture for attaching said assembly to said container, the assembly further comprising:
 attachment means for attaching said filtering device on said container such that the filtering screen is totally immersed in said process fluid,
 flow means for establishing a pressure differential through said filter surface for causing said process fluid to flow from the retentate side of said surface to said withdrawing means, the free clearance around said retentate side of said portion of said surface being such that free access of said process fluid supply to said portion of said filter surface is provided.

In the currently preferred embodiment of the combination according to the present invention said attachment means comprise a fluid lock mechanism having a compartment for receiving and isolating said filtering screen from said process fluid, the compartment communicating with one or more apertures allowing access to said screen for cleaning and maintenance of said filtering screen.

Having a fluid lock mechanism enables easy cleaning and maintenance of the filtering screen without disconnecting it from the assembly, thereby preventing any potential contamination of the process fluid or uncontrolled release of process fluid from the container during cleaning or maintenance. Furthermore it enables the disconnection of the filtering screen from the container and assembly, with only a minimal disturbance of the conditions prevailing in the process fluid. In addition placing several fluid lock mechanisms in different apertures located at different position on the container enables the withdrawal and filtering of partial volumes of the process fluid representing different locations in the process fluid employing the same filtering device, possibly directly connected to an analytical equipment.

In a particularly preferred embodiment of the present invention the surface of said filtering screen is substantially circular cylindrical.

Having a circular cylindrical filter surface in an assembly according to the present invention will ensure that a substantial part of the process fluid near the filter surface will flow across the filter surface, when this is rotated, i.e. a circular cylindrical filter surface is especially suited for enabling cross flow filtration and thereby for preventing filter clogging.

In addition the present invention relates to a cross flow filtering device comprising:
 a filtering screen mounted on and at least partially surrounding a filter body and communicating with one or more first fluid conduits in said body,
 a shaft with a first end and a second end and provided with one or more longitudinal second fluid conduits extending from said first end to said second end,
 said filter body being mounted on the first end of said shaft, such that said first fluid conduits in said filter body communicate with said second fluid conduit in said shaft,
 the second end of said shaft being connected to rotating means for rotating said shaft around the axis thereof, whereby at least a substantial area of the surface of said filtering screen moves at a predetermined tangential speed, and
 withdrawing means communicating with said second fluid conduit at said second end of said shaft for withdrawing the filtered process fluid from said filter body through said second fluid conduits of said shaft, wherein the area and the pore size of said filtering screen and each of said fluid conduits are dimensioned so as to provide a linear velocity of the fluid through the filtering screen which is less than said predetermined tangential speed at a desired flow of filtered process fluid so as to ensure a cross flow velocity of fluid along the surface of a said filtering screen.

In the currently most preferred embodiment of the filtering device according to the present invention said predetermined tangential speed is at least approx. 0.3 meters/second, preferably approx. 0.4 meters/second, more preferably approx. 0.5 meters/second, even more preferably approx. 0.6 meters/second, even more preferably approx. 0.7 meters/second, even more preferably approx. 0.8 meters/second, even more preferably approx. 0.9 meters/second and even more preferably approx. 1.0 meters/second.

Advantageously, the difference between said linear velocity of fluid and said tangential speed is at least approx. 0.2 meters/second, preferably approx. 0.3 meters/second, more preferably approx. 0.4 meters/second, even more preferably approx. 0.5 meters/second, even more preferably approx. 0.6 meters/second, even more preferably approx. 0.7 meters/second, even more preferably approx. 0.8 meters/second, even more preferably approx. 0.9 meters/second, and even more preferably approx. 1.0 meters/second.

Finally, in a preferred embodiment of the filtering device according to the present invention, it further comprises a recirculation fluid conduit for recirculating filtered process fluid to the process fluid.

Having a recirculation fluid conduit for recirculating filtered process fluid to the process fluid, makes it possible to return any unused filtered process fluid to the process, thereby minimizing the potential disturbance of the conditions prevailing in the process fluid posed by the removal of filtered process fluid.

In addition the present invention relates to a fluid lock mechanism for use in a combination according to the present invention and comprising:
 a housing having attachment means for attaching same to the container wall, the housing comprising a first aperture communicating with the aperture in the container wall, a compartment for receiving the filtering screen, and having fluid communication with said first aperture a valve arranged between said first aperture and said compartment for interrupting the communication between said first aperture and said compartment, said valve being adapted to allow passage of said filtering screen from said first aperture to said compartment, at least a second aperture communicating with said compartment for allowing introduction and removal of a cleaning fluid to said compartment.

Having a fluid lock mechanism like the above, makes it possible to mount the assembly of the present invention anywhere on any container provided with an aperture according to the present invention. In addition placing several fluid lock mechanisms in different apertures located at different position on the container enables the withdrawal and filtering of partial volumes of the process fluid representing different locations in the process fluid employing the same filtering device, possibly directly connected to an analytical equipment.

BRIEF DESCRIPTION OF THE DRAWINGS

FIG. 2 shows a schematic, partially sectional view of the preferred embodiment of the shaft and casing according to the present invention shown in FIG. 1.

FIG. 3 shows an enlarged scale schematic, partially sectional view of a preferred embodiment of a filtering screen and a filter body according to the present invention shown in FIG. 1.

FIG. 3a shows a cross section of the filter body shown in FIG. 3 taken along line A-A.

FIG. 4 shows an exploded view of a second embodiment of part of the filtering device according to the present invention FIG. 4a shows a cross section of the filter body shown in FIG. 4 taken along line B-B.

DETAILED DESCRIPTION OF THE INVENTION

At present measurements of parameters reflecting the metabolic state of biological processes, such as waste water treatment and biological gas production, are only used to a limited extent. One of the facts preventing an abundant use of such measurements is that most applicable analytical methods and equipment depend on a filtration of the process fluid. In the present context this offers a series of problems, since these process fluids tend to have a high content of organic fibers, inhomogenous particles, and dissolved fats, which gives them wearing and clogging properties that makes them unsuitable for traditional and proper membrane filtration. In addition, the high content of inhomogenous particles in these process fluids, makes it difficult to remove all particles with a diameter larger than acceptable for most analytical equipment through continuous one-step filtration, without employing very large quantities of process fluid, which would make any method uneconomical. Accordingly, the present invention provides an assembly for simultaneously withdrawing and filtering a partial volume of a process fluid containing particles having an average diameter from about 0.1% to about 1% of the desired average linear flow of withdrawn filtered process fluid through the filtering screen pr. second. A better understanding of the present invention will be provided by reference to the drawings.

Figure 1:
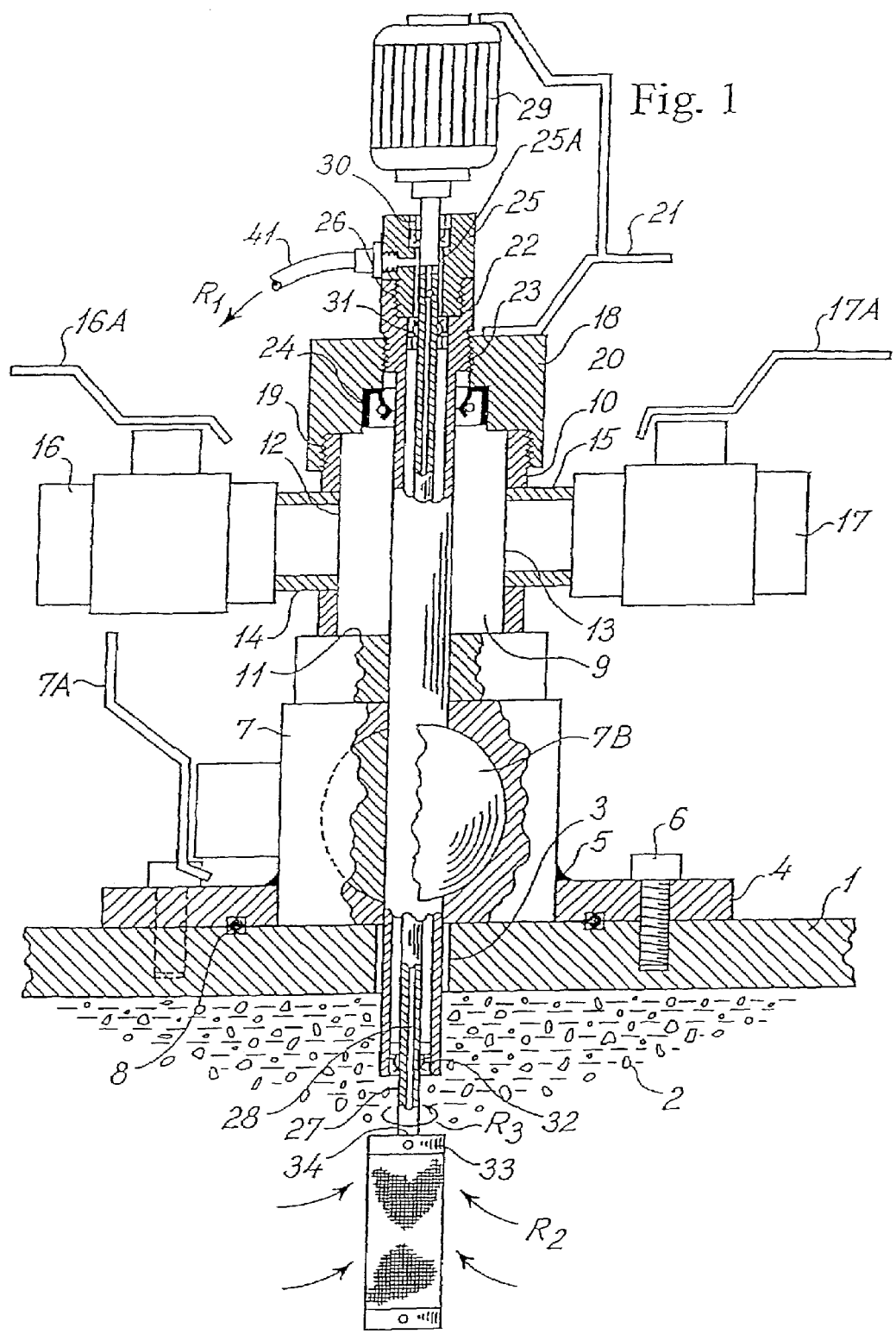
FIG. 1 shows a schematic, partially sectional view of a preferred embodiment of an assembly according to the present invention attached to a container holding a process fluid.

A detailed description of the preferred embodiment of an assembly according to the present invention attached to a container holding a process fluid is provided below with reference to FIGS. 1–3. A wall 1 of a container enclosing a process fluid containing inhomogenous particles 2 is provided with a circular aperture 3 in order to establish fluid communication between the process fluid in the container and the assembly attached to the container.

The assembly is fixed to the container by welding it to a plate 4 at 5. The plate 4 is secured to the container wall by bolts 6. Fluid communication is established between the aperture 3 in the container and a valve 7 having a handle 7A. An O-ring 8 ensures that process fluid can not leak from the container. The valve 7 is, as indicated at 7B, a spherical valve (EGO, Industri Armatur, Denmark, Type 2006 SS-TN 63) and is arranged between the aperture 3 in the container and a compartment 9 having a wall 10 with four apertures, of which the first aperture 11 ensures communication between the valve 7 and the compartment 9. The compartment 9 is circular cylindrical. The second and the third apertures 12 and 13 respectively, in the compartment wall 10 provide unhindered fluid communication between the compartment 9 and two pipe stubs 14 and 15. The two pipe stubs 14 and 15 are each connected to a spherical valve 16 and 17, respectively having handles 16A and 17A, respectively. A cover cap 18 is at 19 threaded on the wall 10 of the compartment 9 around the aperture 17. The cover cap 18 is provided with a handle 21.

A casing 22 having a circular cross section is threaded into the cap 18 at 23, and a lip seal 24 arranged in the cap 18 abutting the casing 22 ensures that process fluid can not leak from the compartment 9. The casing 22 has an enlarged diameter at the end threaded into the cap 18, thereby allowing an insert 25 to be threaded into the casing 22 at 26. A shaft 27 is provided with a longitudinal fluid conduit 28, and connected to an electrical motor 29 of known kind. The shaft 27 is mounted in the casing 22 and the insert 25 by means of three bearings 30, 31 and 32, respectively. The casing 22 enclosing the shaft 27 extends from the cap 18 through the compartment 9, the valve 7 and the aperture 3 into the container. The end of the shaft 27 opposite the electrical motor 29 is threaded into a filter body 33 at 34 as shown in FIG. 1 by means of threads 34A and 34B as shown in FIGS. 2 and 3 respectively. Within the casing the bearings 30, 31 and 32, are sealed by means of lip seals 35, 36 and 37, respectively.

The shaft 27 is further provided with a fluid conduit 38 with a circular cross section establishing fluid communication between the longitudinal fluid conduit 28 in the shaft and the interior 25A of the insert 25. The fluid conduit 28 ends at 28A beyond which the shaft 27 is solid. The insert 25 is provided with a fluid conduit 39 having a thread 40 and establishing fluid communication between the interior of the insert 25A and a tube 41 through which filtered process fluid can be withdrawn as indicated by arrow $R_1$ by known pumping means (not shown).

The filter body 33 threaded to the shaft 27 at 34 (note that FIG. 3 is shown in enlarged scale relative to FIG. 1) is partially surrounded by a filtering screen 42. The filtering screen 42 is mounted on the filter body 33 on top of a supporting net 43 providing the filtering screen 42 with substantial strength, abrasion resistance and stiffness. The filtering screen 42 and the supporting net 43 are fixed on two metal rings 44 and 45. One of the rings 44 comprises a cap 46 provided with an aperture 34C enabling the filtering screen 42 to be fitted on the shaft 27 along with the filter body 33. The filter body 33 comprises radial fluid conduits 47A communicating with the filtering screen and a longitudinal fluid conduit 47B communicating with the radial fluid conduits 47A and the longitudinal fluid conduit 28 in the shaft 27 threaded to the filter body 33.

The radial fluid conduits 47A have a circular cross section. The filter body 33 further comprises a threaded aperture 48 closed by a threaded plug 49. Each end of the filter body further comprises an O-ring 50 and 51, respectively, which is tightly fitted to the two rings 44 and 45 holding the supporting net 43 and the filtering screen 42.

FIG. 3a shows a cross section of the filter body shown in FIG. 3 along the line A—A. This cross section illustrates the communication between the centrally placed longitudinal fluid conduit 47B in the filter body 33 and the radial fluid conduits 47A, facing the outside of the filter body and communicating with the filtering screen 42.

The table below provides ranges of corresponding dimensions and working conditions, for the assembly according to the present invention.

Preferred Embodiments of the Present Invention automatically by a pressure sensor connected to a PLC/PC or a mechanical relay connected to the pump (not shown) withdrawing process fluid through the assembly.

In order to obtain stable operation of the assembly according to the present invention, the filtering screen 42 and the filter body 33 of the filtering device has to be rotated by the electrical motor 29 (see FIG. 1), so as to provide a resulting cross flow velocity of the fluid flowing across the filter surface, $v_1$, of the filtering screen 42, larger than at least approx. 0.5 meters/second to at least 1.0 meters/second. Furthermore, the linear flow of process fluid through the filtering screen 42, indicated by arrow $R_2$ in FIG. 1, must be adjusted so as to provide a stable pressure loss across the filtering device. Any potential clogging of the filtering device can be reversed by reversing the pump flow or possibly employing a second pump for backflushing with filtrate or water.

Alternatively a bladder filled with filtrate placed in a chamber connected to a source of pressurized air can provide a reverse flow of filtrate through the filtering device. This bladder can be filled under the control of a valve, which slowly equalizes the pressure between the chamber and the outside atmospheric pressure. Optionally the rotational velocity can be increased while backflushing.

A linear flow of filtrate through the filtering screen constituting approx. 60 to approx. 80% of the critical upper value during operation will ensure that filter clogging is avoided if the assembly is employed in process fluids containing inhomogenuous particles. From the above it will

| | | | |
|---|---|---|---|
| Filtering screen 42 area | 10–50 cm² | 50–100 cm² | 100–300 cm² |
| Filtering screen 42 diameter | 1–2 cm | 2–3.5 cm | 3.5–5 cm |
| Filtering screen 42 length | 4–8 cm | 8–15 cm | 15–25 cm |
| rotation speed RPM | 1000–2000 | 600–1000 | 400–600 |
| Shaft 27 int. diameter | 4 mm | 4–8 mm | 8–11 mm |
| Shaft 27 ext. diameter | 8 mm | 8–12 mm | 12–15 mm |
| Lip seal 24, 35–37 diameter | 8–22 mm | 8–22 mm | 8–35 mm |
| Combined casing 22 and insert 25 length | 26–30 cm | 30–35 cm | 35–55 cm |
| Casing 22 diameter | 28–30 mm | 28–40 m | 40–45 mm |
| Valve 7 diameter | 1½–2 inch | 2–2½ inch | 2½–3 inch |
| Compartment 9 length | 8–12 cm | 12–20 cm | 20–30 cm |
| Combined volume of conduits 47A and 47B | 5–10 ml | 10–40 ml | 40–140 ml |

Operation of the combination of the container holding a process fluid supply and an assembly, comprising attachment means and a filtering device according to the present invention described above is discussed below. Operating the assembly comprises withdrawing filtered process fluid through the filtering screen 42, as indicated by the arrow $R_2$ in FIG. 1, through the filtering device attached to the container holding the process fluid by the attachment means, and out of the assembly and into the tube 41, as indicated by arrow $R_1$ on FIG. 1, while at the same time rotating the shaft 27, the filter body 33 and the filtering screen 42 as indicated by arrow $R_3$ on FIG. 1. When in use, the flow of filtered process fluid withdrawn through the filtering device, $R_1$, is adjusted so as to provide a stable pressure loss across the assembly. Depending on the nature of the process fluid, the rotation velocity and the dimensioning of the filtering device will determine an upper critical linear flow of filtrate, which provides the largest possible pressure drop across the filtering device. If this critical flow is surpassed the velocity of the fluid flowing tangentially across the filtering screen will not be sufficient to keep the filtering screen free from clogging, resulting in a pressure loss. This can be monitored be understood that in order to prevent clogging of the filtering screen it is crucial to ensure that the resulting cross flow velocity of the process fluid across the filter surface, $v_1$, of the filtering screen 42 is high enough to prevent clogging of the filter pores. This velocity, $v_1$, is a result of the tangential velocity of the filter surface, $v_2$, when rotated in the process fluid, the fluid viscosity, the fluid particle content, and the linear velocity of the fluid through the filtering screen, $v_3$, at the desired flow of filtered process fluid. This complex relationship can be illustrated in a simplified form by formula (I):

$$\underline{v_1} = \alpha * (\underline{v_2} + \underline{v_3}) \qquad (I)$$

Formula (I) describes that the resulting cross flow velocity vector, $\underline{v_1}$, describing the movement of the process fluid across the filter surface can be found by adding the two velocity vectors $\underline{v_2}$ and $\underline{v_3}$ and multiplying the result by a numerical factor, $\alpha$, determined by the physical properties of the process fluid. It seems reasonable to assume that to obtain a substantial cross flow across the filter surface the tangential velocity of the filter surface, $\underline{v_2}$, and the resulting cross flow velocity of the process fluid across the filter surface, $v_+$, have to be operating in closely related planes. Hence, when operating with numerical velocities, it seems reasonable to conclude empirically that to obtain a sufficiently large resulting cross flow velocity across the filter surface, the filtering screen 42 filter body 33 and shaft 27, described above are rotated by the electrical motor 29, as to provide a tangential velocity of the surface exceeding the linear velocity of the fluid through the filtering screen at the desired flow of filtered process fluid. Accordingly, in a preferred embodiment of the present invention the filtering screen 42 filter body 33 and shaft 27 are rotated by the electrical motor 29, at a velocity of approx. 400 to approx. 2000 RPM, most preferably at a velocity providing a tangential velocity of the surface larger than at least approx. 0.3 to at least approx. 1.0 meters/second and a difference between the tangential velocity of the surface and the linear velocity of the fluid through the filtering screen at least approx. 0.2 meters/second to at least 1.0 meters/second at the desired flow of filtered process fluid.

In order to fulfill the requirements concerning the fluid flow through the filtering screen, $v_3$, compared to the flow across it, $v_1$, the currently preferred embodiment of the assembly according to the present invention has been carefully constructed and dimensioned as to provide the desired relationship between $v_1$ and $v_3$. This has been done by:

making use of a circular cylindrical filtering screen 42 with and a pore size of about 35 to about 200 μm, a diameter of approx. 1 to approx. 5 cm, and a length of approx. 4 to approx. 25 cm resulting in a filter area of approx. 10 to approx. 300 cm$^2$, constructing the radial fluid conduits 47A facing the exterior of the filter body and communicating directly with the filtering screen 42 with a circular cross section and a diameter of at least approx. 1 mm to approx. 11 mm to provide a cross sectional area approx. 20 to approx. 100 times the pore size of the filter surface and placing them with a mutual distance within the filtering area which is less than approx. 5 to approx. 15 cm to provide a mutual distance between them which is less than about 10 times the material thickness of the two rings 44 and 45 to which the filtering screen and the filter body are fixed, thereby resulting in a linear fluid velocity through the filtering screen, indicated by arrow $R_2$, not exceeding about 0.5 m/s, with the desired flow of filtered process fluid through the filtering device, placing the bearings 30 and 32, with a mutual distance larger than about half the distance between the end of the casing 22 opposite the electrical motor 29, and the filter body 33 thereby avoiding vibrations during operation/rotation, and at the same time placing the bearings 30, 31 and 32 with the smallest possible mutual distance in order to minimize the dead volume of the casing, constructing the fluid conduits 38 and 39, with a circular cross section and a diameter of approx. 4 to approx. 11 mm, i.e. dimensioning them corresponding to the dimensioning of the longitudinal fluid conduit in the shaft 28, thereby enabling a resulting linear fluid flow rate through the filtering screen 42 not exceeding about 0.5 m/s, when the desired flow of filtered process fluid is withdrawn, dimensioning the insert 25 and the shaft 27 so as to ensure that the difference 25A, between the internal diameter of the insert 25, and the diameter of the shaft 27 between the bearings 30 and 31 or 32 of approx. 4 to approx. 33 mm, i.e. at least 3 times the diameter of the longitudinal fluid conduit 28 in the shaft 27, placing the bearings 30, 31 and 32 with a mutual distance larger than about half the distance between the filter body 33 and the end of the casing 22 opposite the electrical motor 29.

To facilitate operation of the assembly according to the present invention, the attachment means described above have been carefully constructed and dimensioned as to provide an assembly enabling easy cleaning and maintenance of the filtering screen according to the present invention without disconnecting it from the assembly, thereby preventing any potential contamination of the process fluid or uncontrolled release of process fluid from the container during cleaning or maintenance of the filtering screen. Furthermore the preferred attachment means according to the present invention enables the disconnection of the filtering screen from the assembly, with only a minimal disturbance of the conditions prevailing in the process fluid in the container. In addition placing several attachment means in different apertures located at different position on the container enables the withdrawal and filtering of partial volumes of the process fluid representing different locations in the process fluid employing the same filtering device, possibly directly connected to an analytical equipment. This has been obtained by constructing the filtering screen 42, filter body 33 and connecting shaft 27 in such a way, that they can easily be withdrawn from the container holding the process supply and into the compartment, 9, and cleaned by the use of a cleaning fluid, i.e. by:

constructing the valve 7 as a spherical valve, which when open has an internal diameter of about 4 to about 8 cm or about 1 to about 3 inch, thereby allowing the filtering device pass through it, constructing the compartment, 9, as a circular cylinder with an internal diameter of about 4 to about 8 cm or about 1 to about 3 inch and a length of about 8 to about 30 cm, i.e. about 2 to about 4 cm longer than the sum of the length of the filter body 33 and the distance between the filter body 33 and the end of the casing 22 opposite the electrical motor 29, thereby allowing the filtering device to pass through the valve, 7, and into the compartment, 9, without being blocked by precipitated particles from the process fluid, fitting the two pipe stubs, 14 and 15, to spherical valves, 16 and 17 respectively, having an internal diameter about 2 to about 4 cm or about ½ to about ½ inch, i.e. about half the diameter of the first valve, 7, thereby when open allowing the removal of precipitated materials from the process fluid trapped in the fluid lock mechanism, constructing the two metal rings 26 and 27 with a material thickness of about 0.5 to about 1.5 mm and a diameter of approx. 1 to approx. 5 cm, constructing the filter body 33, so that the second end of same comprises a threaded aperture 48, communicating with the fluid conduits 47A and 47B, in the filter body, which facilitates cleaning and maintenance of the filter body 33, constructing the casing 22 with a circular cross section and an external diameter of approx. 2 to approx. 5 cm, i.e. an external diameter larger than the diameter of the filter body 33, thereby enabling the removal of the filtering screen 42 and filter body 33, from the process fluid without disconnecting the attachment means, and providing the cap 18 with the handle 21, which potentially prevents any dislocation of the insert, 25, casing 22, filtering screen 42, and filter body 33, if pressure builds up in the process system, while the assembly of the present invention is being operated.

FIG. 4 shows an exploded view of an alternative embodiment of part of the filtering device according to the present invention. In this embodiment of the filtering device according to the present invention, a filtering screen 42 with a circular cylindrical filter surface is mounted on and partially surrounding a filter body 33 provided with a total of 16 radial fluid conduits 47A communicating with the filtering screen 42, and all communicating with a longitudinal fluid conduit 47B. The filter body 33 is mounted on the first end of a shaft 27 provided with one longitudinal fluid conduit 28, extending through the shaft, such that the longitudinal fluid conduit in the filter body 47B is communicating with the fluid conduit 28 in the shaft 27. The second end of the shaft 27 is mounted in a casing 22 through which the fluid conduit of the shaft is communicating with withdrawing means for withdrawing filtrate similar to the ones comprised in the assembly described above with reference to FIGS. 1, 2 and 3. The filtering screen 42 filter body 33 and part of the connecting shaft 27 are immersed in the biological process fluid to be filtered by the use of attachment means similar to the ones comprised in the assembly described above with reference to FIGS. 1, 2 and 3, and the filtering screen 42 filter body 33 and shaft 27 are rotated around the axis thereof in said biological process fluid by a rotating driving mechanism similar to the electrical motor described above with reference to FIG. 1 at approx. 400 to approx. 2000 RPM. The filtering screen 42 filter body 33 fluid conduits 47A, 47B and 28, and casing 22 of this preferred embodiment of the invention are in principle dimensioned according to the description of these parts provided above with reference to FIGS. 1, 2 and 3, except from the fact that the number of fluid conduits communicating with the filtering screen 42 is different in this embodiment, compared to the number of fluid conduits communicating with the filtering screen 42 in the embodiment described above with reference to FIGS. 1–3.

FIG. 4A shows a cross section of the filter body shown in FIG. 4 along the line B—B. The cross section B—B through the filter body shown in FIG. 4A as the cross section A—A shown in FIG. 3A visualizes the communication between a centrally placed longitudinal fluid conduit in the filter body and the radial fluid conduits 47A facing the outside of the filter body and communicating with the filtering screen 42. It should be noted, that when compared to FIG. 3A the radial fluid conduits 47A facing the outside of the filter body shown in FIG. 4A differ with regards to their cross sectional area.

When comparing FIGS. 3 and 3A to FIGS. 4 and 4A, a total of 8 radial conduits 47A facing the outside of the filter body 33 and communicating with the filtering screen 42 are indicated in the filtering device shown in FIGS. 3 and 3A, while a total of 16 conduits are indicated in the filtering device shown in FIGS. 4 and 4A. In combination this reflects the fact that the radial fluid conduits 47A preferably, as also described above, should be dimensioned as to provide a resulting linear fluid velocity through the filtering screen not exceeding about 0.5 m/s, with the desired flow of filtered process fluid through the filtering device, i.e. it reflects that when having the same desired flow of filtered process fluid and essentially the same filtering screen 42 and longitudinal fluid conduits 47B and 28 in the filter body 33 and the shaft 27 respectively, then the fewer the radial fluid conduits 47B facing the outside of the filter body and communicating with the filtering screen 42 the larger these should be.

In another embodiment of the present invention the insert 25 is provided with a recirculation fluid inlet (not shown), which allows filtered process fluid to be returned to the container holding the process fluid.

In yet another embodiment of the present invention the filtering screen 42 has pore size of less than about 35 μm. In this case the filtering screen 42 has a thickness of about 2 to about 6 mm and a pore size on the outside, which is slightly smaller than the pore size on the inside, thereby providing the best possible flow of filtrate, and is made from a ceramic or polymer material providing a substantial strength, abrasive resistance and stiffness to resist acidic and alkaline conditions in the pH range from about 2 to about 10 similar to that of stainless steel or plastic. The filter body 33 is made according to the instructions provided above except that it comprises an end piece extending about 0.1 to about 0.5 mm in addition to the filter thickness from the filter body, thereby providing support for a lipseal and the filtering screen 42. Furthermore the filter body 33 in this case is provided with a bottom ring/plate having the same external diameter as the end piece and with a threaded aperture similar to 48.

EXAMPLES

Example 1

Filtration Test

A test was conducted on an assembly constructed according to the present invention having the dimensions provided in the table below and operated under the conditions provided in the table below.

Description of Assembly Used

| | |
|---|---|
| Filter surface area | 31 cm$^2$ |
| Filtering screen diameter | 2 cm |
| Filtering screen length | 5 cm |
| RPM | 1000–2000 |
| Connecting shaft | 8 mm ext. dia., 4 mm mt. dia. |
| Casing fittings | 22 mm ext. dia. |
| Casing length | 30 cm, 30 mm ext. dia. |
| Fluid lock mechanism tube/Vents | 1½–2 inch |
| Fluid lock mechanism tube length | 12 cm |
| Filter body dead volume | 10 ml |

The filtering screen, filter housing and connecting shaft were rotated using a variable motor with a digital speed display (Heidolph RZR 2051). The assembly was fitted to a 4.5 l fermenter with temperature control. Cow manure having a composition as listed in the table below and digested manure having a composition as listed in the table below were used as process fluids.

Composition Description of Manure Used

| Component | Cow manure | Reactor effluent |
|---|---|---|
| TS | 87.4 g/l | 37.1 g/l |
| VS | 63.7 g/l | 27.5 g/l |
| Kjeldahl N | 4.08 g-N/l | 2.45 g-N/l |
| pH | 7.09 | 7.41 |
| Insoluble Carbohydrates | 31.7 g/l | 18.0 g/l |
| Dissolved Carbohydrates | 4.76 g/l | 2.76 g/l |

-continued

| Component | Cow manure | Reactor effluent |
|---|---|---|
| Lipids (GTO) | 3.49 g/l | 0.00 g/l |
| Insoluble Proteins (6.63 × Org. bound -N) | 12.82 g/l | 6.70 g/l |
| Amonia/Amonium -N | 2.15 g-N/l | 1.44 g-N/l |
| Acetate | 6.34 g/l | 0.07 g/l |
| Propionate | 2.50 g/l | 0.0 g/l |
| Butyrate | 1.47 g/l | 0.0 g/l |
| Valerate | 0.59 g/l | 0.0 g/l |
| Total volatile fatty acids (VFA) | 10.91 g/l | 0.07 g/l |
| Acetate | 9.72 g/l | 0.07 g/l |
| Carbonate | 3.75 g $CO_2$/l | 7.75 g $CO_2$/l |
| Cat-ions (K+) | 4.13 g/l | 3.09 g/l |
| Phosphoric acid (H2PO4-P) | 0,55* g-P/l | 0,33 g-P/l |

*Average of Danish cow manure

Filtered process fluid was withdrawn through the assembly using a Watson Marlow peristaltic pump 501, and vacuum was monitored using a liquid pressure scale. If the vacuum pressure was less then 0.8 bar the filtering screen was considered irreversible clogged and the flow was reversed before conducting a new test. Filtered process fluid was returned to the fermenter in order to ensure a constant composition.

Figure 5:
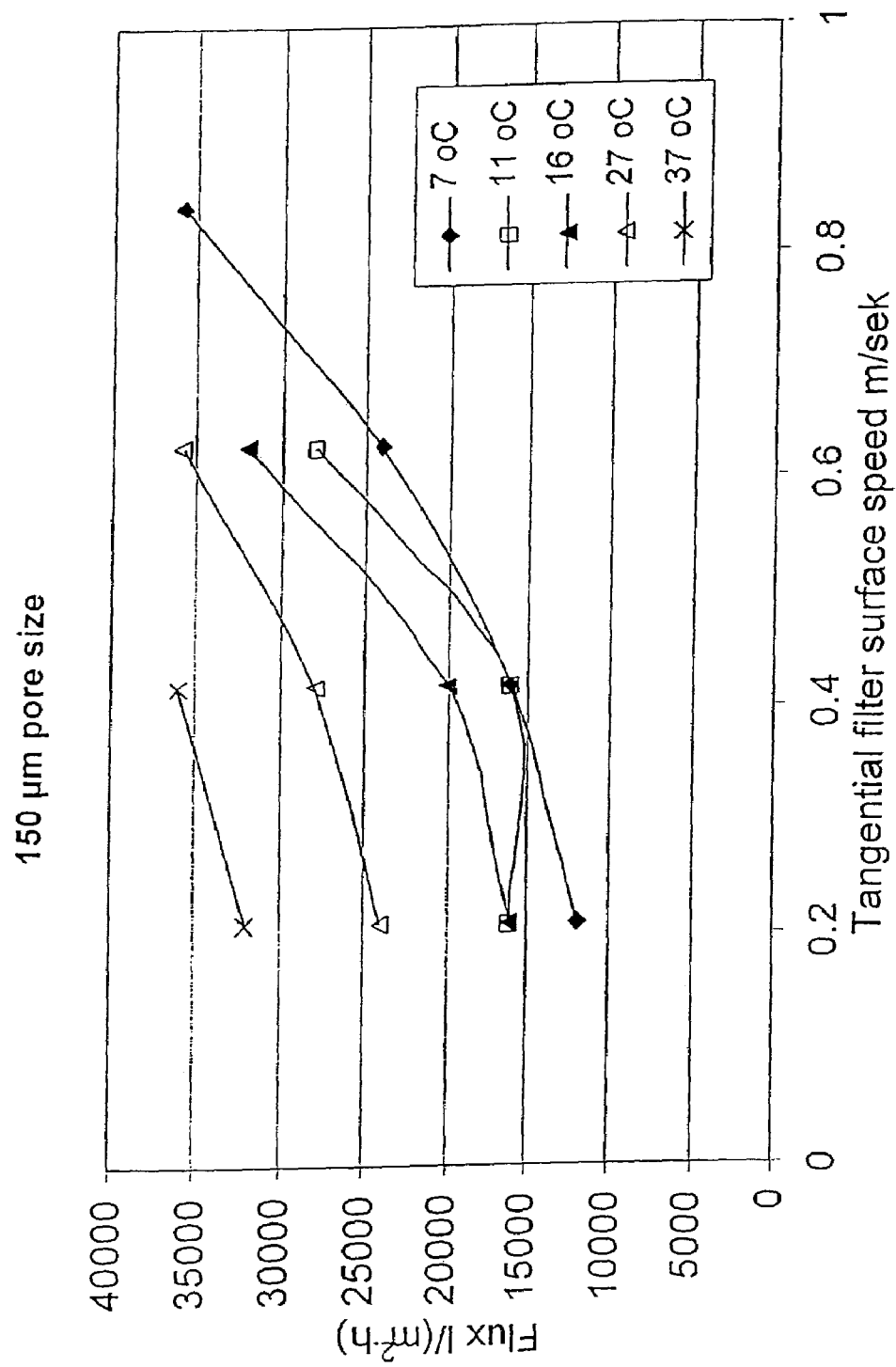
FIG. 5 shows a graph of the results of a maximum flux test using an assembly according to a preferred embodiment of the present invention.

The first test was conducted using a replaceable grid (stainless steel) with a pore size of 150 μm as a filtering screen. All tests were conducted using a mixture of digested manure with a TS content of 37 g/l. The media temperature was changed using the temperature control of the fermenter and the results are shown in FIG. 5.

Figure 6:
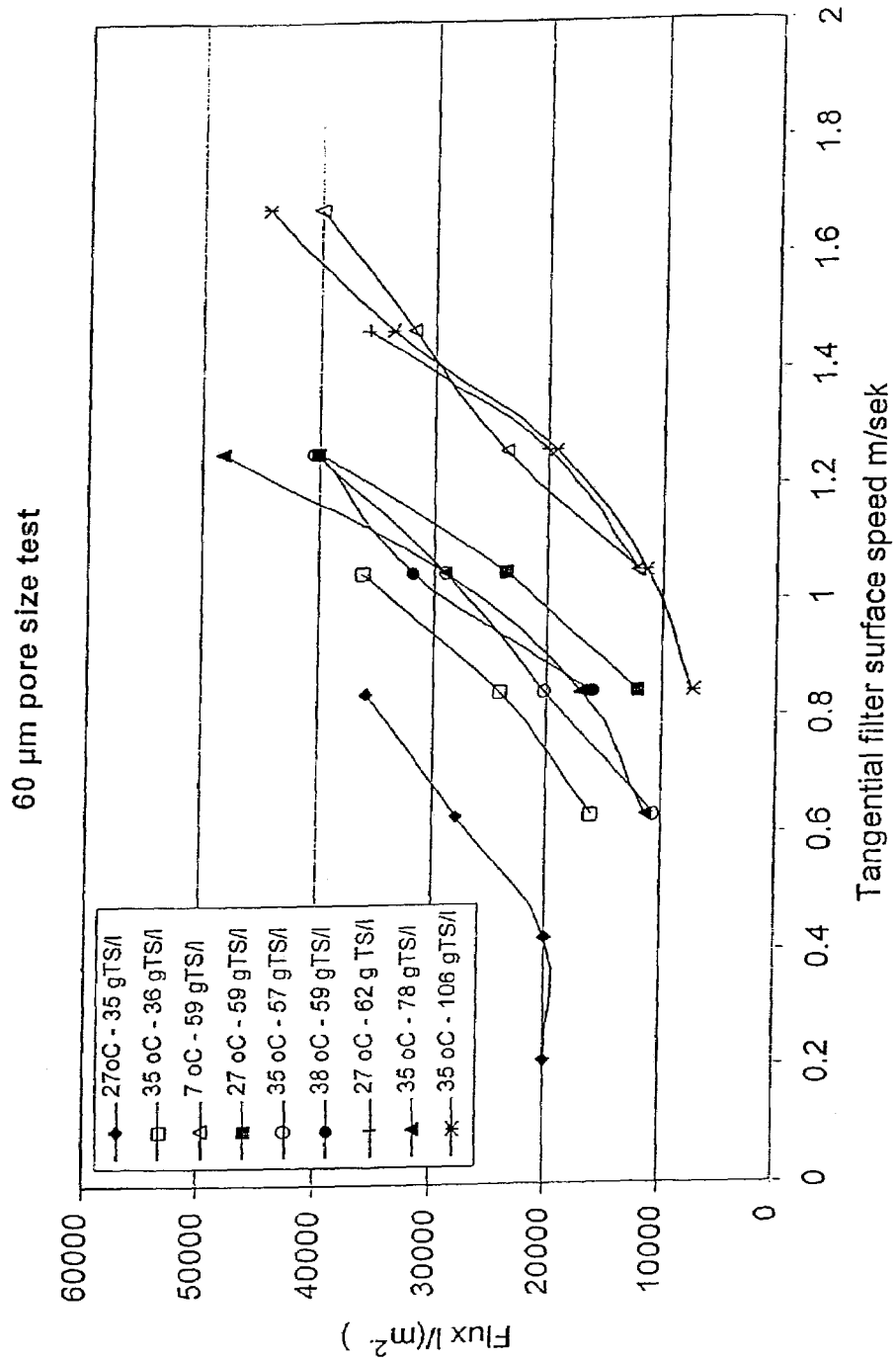
FIG. 6 shows a graph of the results of a maximum flux test using an assembly according to another preferred embodiment of the present invention.

Further tests were conducted using a replaceable grid (stainless steel) with a pore size of 60 μm. All the following tests were in conducted in an active fermenter producing biogas. The reactor temperature was initially 35° C. (mesophilic conditions), but in some cases the temperature was temporarily lowered or increased while conducting the flux test. The reactor was initially feed with a mixture of 60% manure and 40% water resulting in a composition as shown in table 2. The retention time was 15 days. The reactor content initially had a TS content of 35–36 g/l, which was increased by loading 80% manure to the reactor over a period of 4 month. This loading increased the TS content to 59 g/l. To further increase the TS content the reactor effluent was withdrawn using the assembly of the present invention. The filtered process fluid had a TS content of 25–32 gTS/l and the reactor content could thereby be increased over 10 days to 106 g TS/l, for the final test. The result of the flux test is shown in FIG. 6.

Example 2

Consistency Between Filtered and Non Filtered Samples

To evaluate the efficiency of the assembly according to the present invention for continuously withdrawing and filtering process fluid, tests were conducted with variable contents of volatile fatty acids in the fermenter. The content of volatile fatty acids measured in samples taken directly from the reactor was compared with the content measured in samples withdrawn through the assembly of the present invention having the dimensions provided in the table of example 1 and using a filtering screen with a pore size of 60 μm. Samples were acidified using phosphoric acid and centrifuged. The supernatant was then filtered using a syringe filter (1.2 μm) and analyzed on a GC calibrated for measurements of volatile fatty acids. The correlation between the samples taken directly from the reactor and the samples withdrawn through the assembly is shown in FIG. 7.

The volatile fatty acid (VFA) measurements showed excellent correlation between the two sampling methods, when considering that the methods used for sample preparation results in an inaccuracy of at least±5%.

The invention claimed is:

1. A method for withdrawing and filtering a partial volume of a particle-containing process fluid enclosed in a container, the method comprising the following steps:
   providing an aperture in a wall of the container,
   providing a filtering device having a filtering screen having a filter surface and adapted for rotation about an axis of rotation, wherein said surface is rotated around said axis at a speed sufficient to cause at least a substantial area of said surface to move at a tangential speed of at least approx. 0.3 meters/second, withdrawing means for withdrawing filtered process fluid and rotating means for rotating said surface around said axis,
   fixing said filtering device in said aperture such that the filtering screen is immersed in said process fluid,
   establishing a pressure differential through said filtering screen for causing said process fluid to flow therethrough to said withdrawing means, said flow of the process fluid having a linear velocity, and
   rotating said surface around said axis, while ensuring free access of said process fluid to at least a portion of said surface
   and wherein the method does not include a step of relying on a narrow gap between a stationary body and said rotating filter surface
   and wherein the linear velocity of said process fluid through the filtering screen is at least approx. 0.2 meters/second less than said tangential speed
   and wherein the method is used for essentially continuous, on-line filtration of biological process fluids.

2. A method according to claim 1, wherein said surface is rotated around said axis at a speed sufficient to cause at least a substantial area of said surface to move at a tangential speed of at least approx. 0.5 meters/second.

3. A method according to claim 1 further comprising the steps of isolating said filtering screen in said compartment and cleaning said screen with a fluid supplied through one of said apertures, the fluid optionally being made acidic or alkaline by addition of acid or base, respectively.

4. A method according to claim 1 wherein the surface is substantially circular cylindrical.

5. A method according to claim 1, wherein said surface is rotated around said axis at a speed sufficient to cause at least a substantial area of said surface to move at a tangential speed of at least approx. 1.0 meters/second.

6. A method according to claim 5, wherein the difference between said linear velocity of the fluid and said tangential speed is at least approx. 0.5 meters/second.

7. A method according to claim 5, wherein the difference between said linear velocity of the fluid and said tangential speed is at least approx. 1.0 meters/second.

* * * * *